United States Patent
Gagnon

(10) Patent No.: US 6,774,149 B1
(45) Date of Patent: Aug. 10, 2004

(54) HOW TO CONVERT CARBON MONOXIDE INTO SYNTHETIC PETROLEUM BY A PROCESS OF CATALYTIC HYDROGENATION CALLED COPETROLISATION

(76) Inventor: Robert Gagnon, 2875 Descoteaux Street, Sherbrooke, Quebec (CA), J1K 1N7

( * ) Notice: Subject to any disclaimer, the term of this patent is extended or adjusted under 35 U.S.C. 154(b) by 0 days.

(21) Appl. No.: 10/705,526

(22) Filed: Nov. 12, 2003

(51) Int. Cl.[7] ............................................... C07C 27/00
(52) U.S. Cl. ....................................... 518/721; 518/719
(58) Field of Search .................................. 518/719, 721

(56) References Cited

U.S. PATENT DOCUMENTS 3,979,332 A * 9/1976 Kiovsky et al. ................ 502/3
5,763,716 A * 6/1998 Benham et al. ............. 585/315

* cited by examiner

*Primary Examiner*—J. Parsa

(57) ABSTRACT

The process called COpetrolisation uses two catalysts instead of one, converting CO into C7H16. Addition of a NaCl catalyst to a FeO catalyst improves the efficiency of Fischer's process because the salt catalyst retains humidity. Furthermore, chlorine opens chemical chains and sodium prevents crystals of oxygen from covering the FeO catalyst. If we are equipped to produce CO from biogas or smoke and if we want to recycle this unwanted gas, we can COpetrolise this CO and yield a useful liquid. In fact, recycling CO into synthetic crude petroleum, heptane, contributes to clean air and to produce a valuable source of energy. Because CO is a renewable resource, COpetrolisation favors a lasting economic development.

4 Claims, No Drawings

HOW TO CONVERT CARBON MONOXIDE INTO SYNTHETIC PETROLEUM BY A PROCESS OF CATALYTIC HYDROGENATION CALLED COPETROLISATION

FIELD OF THE INVENTION

The present invention is directed to a process for producing hydrocarbons from carbon monoxide, in particular, to a process for producing synthetic crude petroleum from carbon monoxide by catalytic hydrogenation.

BACKGROUND OF THE INVENTION

Converting carbon monoxide into synthetic petroleum by catalytic hydrogenation is a process invented by M. Fischer and. M. Tropsch during the twenties and thirties. As M. Bergius at the same time, they used an iron catalyst to produce hydrocarbons. In 1925, Fischer-Tropsch produced a real industrial synthesis of hydrocarbons and oils under normal pressure with a cobalt catalyst and thorine. These processes were improved in 1930 and during world war 2 using nickel and nickel-cobalt catalysts. The Fischer-Tropsch process was also applied in England by the Synthetic Oil Cy Ltd using cobalt and thorium catalysts. Other companies Improved the Fischer-Tropsch process using costly alloy catalysts without succeeding to eliminate problems of instability due to the presence of oxygen, humidity or water vapor in the reactor. See canadian patents no. 360,194, no. 411,979, no. 556,715 and no 559,476.

SUMMARY

There are many processes converting carbon monoxide into liquid synthetic petroleum. Everybody knows that catalytic hydrogenation is feasible but its efficiency is problematic mostly because of the instability due to the unavoidable presence of oxygen and water vapor in the reactor. We also know that catalysts act as accelerators or as decelerators in chemical reactions without being part of the finished products. In converting carbon monoxide into liquid synthetic petroleum by catalytic hydrogenation, the use of an iron catalyst or other similar catalysts necessitates many manipulations which may affect expected output. COpetrolisation brings in a second catalyst, salt, which retains humidity. Furthermore, chlorine opens chemical chains and sodium prevents crystals of oxygen from covering the iron catalyst. Doing so, the salt catalyst improves the action of the iron catalyst. Catalytic hydrogenation of carbon monoxide becomes more regular and easier to standardize. COpetrolisation of carbon monoxide regularly produces 55% water and 45% heptane.

DETAILED DESCRIPTION

Many sources of carbon monoxide has been experienced: for example, blogas, smoke, etc. are fundamental sources of CO and raw materials for future processing by COpetrolisation. Everybody also knows that we can have carbon monoxide from carbon dioxide by the chemical formula: $CO_2+C=2CO$ where carbon, C, is red hot coal. Another possibility could be burning organic matters in the presence of a small quantity of oxygen in order to produce the greatest quantity of carbon monoxide.

Catalysts used in COpetrolisation are an iron catalyst, Feo, and a salt catalyst, NaCl. These two catalysts must be powdery or crushed to a size a diameter less than 1 mm. For the required quantity of these catalysts, we must know the capacity of the reactor. In general, we use about 2 parts of salt for 1 part of iron in other words about 6%–10% wt. of salt and about 3%–5% wt. of iron. Because catalysts are not part of the finished products, it is not necessary to have definite quantities of each catalyst but it is important to have more salt than iron, 2 times more is a good approximation. These proportions come from the specific action of each catalyst: the iron catalyst makes possible the synthesis of carbon and hydrogen when the salt catalyst retains humidity. Furthermore, chloride opens chemical chains and sodium prevents crystals of oxygen from covering the iron catalyst. These catalysts must be mixed before putting them in a reactor.

We put the iron-salt catalyst into a reactor covering the largest area inside this reactor. Into the reactor, we blow 2 gases, carbon monoxide and hydrogen, according to proportions already defined in the Fischer's formula: $7\ CO+15\ H_2=C_7H_{16}+7\ H_2O$ in other words about 87% carbon monoxide+13% hydrogen for an appropriate result of about 44% heptane and about 56% water. We heat up to a constant inside temperature of about 160° C.–200° C. without exceeding 200° C. in order to avoid formation of methane or other alcanes. While heating at constant temperature, we maintain inside gases at constant pressure of about 2200 p.s.i.–3000 p.s.i. as long as COpetrolisation is progressing, in other words during less than about 30 minutes. The whole process of COpetrolisation works more effectively if the reactor is shaked because action of catalysts are improved. When chemical reactions of COpetrolisation are finished, we extract the heptane-water mixture and we filter it to separate heptane from water.

What is claimed is:

1. A process for producing heptane by the reaction of an hydrogen gas with a carbon monoxide in the presence of a catalyst being made up of about ⅓ of crushed iron, FeO, and about ⅔ of crushed salt, NaCl, caracterised by the circulation of an hydrogen gas and a carbon monoxide in the presence of this iron-salt catalyst at a constant temperature of about 160° C.–200° C., at a constant pressure of about 2200 p.s.i.–3000 p.s.i. during about 30 minutes.

2. A process as defined in claim 1, in which an iron catalyst and a salt catalyst to be used are FeO and NaCl.

3. A process as defined in claim 1, in which an iron catalyst and a salt catalyst to be used are crushed to a size a diameter less than about 1 mm.

4. A process as defined in claim 1, in which an iron catalyst and a salt catalyst to be used are mixed in proportion to about 1 part of iron for about 2 parts of salt.

\* \* \* \* \*